United States Patent [19]
Knight

[11] Patent Number: 5,391,205
[45] Date of Patent: Feb. 21, 1995

[54] TRACHEOESOPHAGEAL VOICE PROSTHESIS

[76] Inventor: Roy F. Knight, P.O. Box 1516, Norman, Okla. 73070

[21] Appl. No.: 809,665

[22] Filed: Dec. 17, 1991

[51] Int. Cl.$^6$ .................. A61F 2/20; A61M 16/00; A62B 9/06
[52] U.S. Cl. .................. 623/9; 128/200.26; 128/207.14; 128/207.16
[58] Field of Search .............. 128/200.26, 203.11, 128/207.14–207.17, 207.29; 623/9; 604/9, 10, 247, 264, 282

[56] References Cited

U.S. PATENT DOCUMENTS

| | | | |
|---|---|---|---|
| 155,667 | 10/1874 | Painter | 137/885 |
| 249,557 | 11/1881 | Truesdell | 137/885 |
| 4,040,428 | 8/1977 | Clifford | 128/351 |
| 4,044,402 | 8/1977 | Edwards | 3/1.3 |
| 4,435,853 | 3/1984 | Blom et al. | 623/9 |
| 4,439,872 | 4/1984 | Henley-Cohn et al. | 3/1.3 |
| 4,596,579 | 6/1986 | Pruitt | 623/9 |
| 4,610,691 | 9/1986 | Depel et al. | 623/9 |
| 4,614,516 | 9/1986 | Blom et al. | 623/9 |
| 4,808,183 | 2/1989 | Panje | 623/9 |
| 4,820,304 | 4/1989 | Depel et al. | 623/9 |
| 4,911,716 | 3/1990 | Blom et al. | 623/9 |
| 5,064,433 | 11/1991 | Blom et al. | 623/9 |
| 5,107,828 | 4/1992 | Koss et al. | 128/200.26 |

OTHER PUBLICATIONS

Mahiew, H. F., "Candida Vegetations on Silicone Voice Prostheses", Arch. Otolaryngol. Head Neck Surg. Mar. 1986, vol. 112, pp. 321–325.

*Primary Examiner*—Randall L. Green
*Assistant Examiner*—Elizabeth M. Burke
*Attorney, Agent, or Firm*—R. William Graham

[57] ABSTRACT

The present invention relates to a tracheoesophageal voice prosthesis device and an insertion tool for the same. The device includes a generally cylindrical tapered housing having a bore therethrough and readily removable valve means operably connected to the housing. The housing has a larger diameter end and a smaller diameter end. The larger diameter end portion includes an inner threaded surface portion which terminates in an inner grooved surface. The valve means includes a check valve and bearings operably disposed adjacent the inner grooved surface and a retainer having a surface portion threaded in a complimentary manner to the inner threaded surface of the housing for retaining the check valve and bearings within the housing when threaded thereto. The insertion tool comprises a generally cylindrical member having one end of a small enough diameter size and of a sufficient length to enable passing the end through the bore of the device and wherein the end is further characterized to have a rounded aspect, and another end of a larger diameter than the bore of the device to prevent passage therein.

9 Claims, 2 Drawing Sheets

TRACHEOESOPHAGEAL VOICE PROSTHESIS

BACKGROUND OF THE INVENTION

1. Field of the Invention

This invention relates generally to a voice prosthesis. More specifically, this invention relates to a tracheal-esophageal voice prosthesis device which allows post-laryngectomy patients having a surgically created tracheostoma and a tracheal-esophageal fistula to produce nearly effortless speech as near to normal as possible.

2. Discussion of Related and Prior Art

The human larynx is susceptible to injury, trauma and various types of diseases such as cancer. It has been known for over 100 years that sounds can be made without the use of the larynx. After removal of the larynx, the patient is known as an laryngectomee and is left with the following three options available for regaining speech:

- Electrolarynx Speech—Wherein the laryngectomee uses a electronic device which produces a generally monotonal output modulated by the vibrations received from a transducer held to the outside of the throat or one which has a tubing placed inside the mouth to produce sounds. This type of speech is easy to learn, but has a rather mechanical sound and the unit must be turned on during speaking and also requires the use of one hand to hold the device. Electrolarynx speech has been judged as the least acceptable of the three types of speech.
- Esophageal Speech—Wherein the laryngectomee must periodically swallow quantities of air and to speak, release the air by regurgitating or burping to allow the air to travel up the esophagus causing the membranes to vibrate sounds and with the aid of the tongue, teeth, and nasal passages, etc., to create speech through the mouth. Esophageal speech is the most difficult of the three types to learn with a success range from 25% to 90%, and in most cases, requires many weeks of expensive voice lessons to master the technique. Esophageal speech has been judged superior to electrolarynx speech.
- Tracheal-Esophageal Speech—Wherein the laryngectomee having a surgically created tracheostoma and a tracheal-esophageal fistula uses a voice prosthesis device that is placed in the trachea and inserted through a tracheal-esophageal fistula into the esophagus. Tracheal-esophageal speech occurs when a finger, thumb, or tracheostoma valve covers the stoma opening outside the neck to divert the exhaled air from the lungs to the trachea and through the prosthesis device into the esophagus while at the same time preventing the esophageal material from entering into the trachea, then the exhaled air travels up the esophagus causing the membranes to vibrate sounds and with the aid of the tongue, teeth, and nasal passages, etc., to create speech through the mouth. Tracheal-esophageal speech is nearer to normal speech and has been judged significantly superior to electrolarynx and esophageal speech.

In order to provide background information so that the invention may be completely understood and appreciated in its proper context, reference now may be made to a number of prior art patents, and publications as follows:

In the past, artificial larynx devices and voice prostheses have been built to accomodate various positions inside and outside the neck. Some of the earlier types housed different types of reed valves and vibrating devices in an effort to reproduce the function of the larynx. Many of these devices were incapable of functioning properly due to saliva drainage from the mouth into the devices, aspiration of esophageal material into the trachea, leakage of the various valves and the valve flapper would herniate beyond the valve seat to mention only a few of the many problems which occurred.

The Henley-Cohn et al. U.S. Pat. No. 4,439,872; Pruitt U.S. Pat. No. 4,596,579; and the Panje U.S. Pat. No. 4,808,183; each illustrate a prosthesis having a rearward end duckbill type valve that extends deeply into the esophagus. Consequently, the rearward end of the duckbill prosthesis at times comes in contact with the rearward wall of the esophagus, thus restricting the air flowing up the esophagus and with its' long extended end within the esophagus, it further impedes the ability to speak; swallowing of food and pills; or drinking liquids. Duckbill prostheses generally have a smaller tubing bore size which minimizes the volume of air flow into the esophagus. Valve leakage of the duckbill type prostheses also occurs more often than with other prostheses.

U.S. Pat. No. 4,435,853 to Blom et al.; U.S. Pat. No. 4,610,691 to Depel et al.; U.S. Pat. No. 4,614,516 to Blom et al.; and U.S. Pat. No. 4,820,304 to Depel et al.; all have a protective hood over the valve or a circumferential extending shoulder which also extends deeply into the esophagus, and like the aforementioned duckbill types, also impede the ability to speak; swallowing of food and pills; or drinking liquids with the extended shoulder of foreign material in the esophagus. The above mentioned prostheses have a one-way valve formed as part of the tubular housing of the prosthesis or one that is cemented within the housing that is non-changeable when valve leakage occurs. All of the past prostheses can be worn for only a few weeks until the one-way valve begins to leak esophageal material into the trachea. Then, the entire prosthesis must be thrown away and a new one installed which is an added expense to the laryngectomee.

U.S. Pat. No. 4,911,716 to Blom et al.; in particular, discloses a surgical implant for use with a voice prosthesis. This implant is left secured to both sides of the tracheal-esophageal fistula and the tubular housing of the prosthesis device is the only part that the wearer can remove to clean or replace when the valve begins to leak. If the implant is left for long periods of time in the patient and an inflamed wall or growth of cancer did occur around the implant, it may go undetected in the fistula since the implant covers this area. The wearer is also restricted in that the implant may be removed only by trained personnel at the hospital or at their office which is also an added expense to the wearer.

Further, many tubular housing prostheses are made from silicone materials that have been found to become contaminated with food particles, mucus, saliva, and certain species of Candida or flora that occasionally infect mucus membranes of the throat and trachea areas. See, Mahieu, H. F., et al., "Candida Vegetations on Silicone Voice Prostheses," Arch. Otolaryngol. Head Neck Surg., Mar. 1986, Vol. 112, pp. 321-325.

Heretofore, voice prostheses have been produced in commercial quantities, with the laryngectomee having a limited selection of only a few types and sizes to fit all. Herein lies the problem, in the same way people require different eye prescriptions or teeth replacement and the like, so should the voice prosthesis be fitted for each individual laryngectomee. Each laryngectomee should be fitted correctly to achieve the best possible vocalization with the least amount of strain or effort to produce speech.

Whatever the precise merits, features and advantages of the above cited references, none of them achieves or fulfills the purposes of the current tracheoesophageal voice prosthesis and insertion tool of the present invention.

SUMMARY OF THE INVENTION

The principle object of the present invention is to achieve a significantly improved tracheal-esophageal voice prosthesis device which makes it possible for post-laryngectomy patients having a surgically created tracheostoma and a tracheal-esophageal fistula to produce nearly effortless speech as near to normal as possible.

It is another principle object of the present invention to provide a tracheal-esophageal voice prosthesis device having a retention collar at the rearward end of the tubular housing extending into the esophagus only enough to retain the prosthesis device in proper position, and thereby does not impede the speaking process, swallowing food and pills, or drinking liquids.

Another object of the present invention is to provide a tracheal-esophageal voice prosthesis device whereby the unique tubular housing and low-pressure valvular design, in combination, permits sufficient quantities of exhaled air flow from the lungs into the esophagus while at the same time prevents esophageal material from entering into the trachea.

Another important object of the present invention is to provide a tracheal-esophageal voice prosthesis device that allows the laryngectomee, without assistance, to easily dilate a small, normal, or misaligned tracheal-esophageal fistula during insertion and prior to removal of the device with the aid of a insertion tool.

A further object of the present invention is to provide a tracheal-esophageal voice prosthesis device wherein the construction material of the tubular housing is such that it is made of non-irritating material and can be used for many years.

Still another object of the present invention is to provide a tracheal-esophageal voice prosthesis device that has an ameliorated one-way check valve assembly within the tubular housing that is removable and replaceable.

Still another important object of the present invention is to provide a tracheal-esophageal voice prosthesis device which permits the valve retainer to be removed and replaced from the tubular housing and also permits the valve bore size to be enlarged or reduced to accomodate to the specific lung capacity of the laryngectomee thereby enhancing the wearers voice.

Still a further object of the present invention is to provide a tracheal-esophageal voice prosthesis device that substantially limits the expelled mucus material of the lungs entering the prosthesis without restricting the air flow through the bore of the tubular housing.

It is another object of the present invention to provide a tracheal-esophageal voice prosthesis device to facilitate an easier and less painful way of inserting and removing the prosthesis device from the tracheal-esophageal fistula which will greatly minimize tearing of the tracheal-esophageal wall thereby reduce bleeding of the fistula during insertion or removal of the device for regular hygiene cleaning or replacement.

It is another object of the present invention to provide a tracheal-esophageal voice prosthesis device which eliminates gluing the device to the neck which causes allergic reactions in some wearers.

Through extensive research and various experiments it has been learned that to permit adequate quantities of air to pass from the lungs to the trachea through the prosthesis device and into the esophagus; the tubular housing bore, the valve bore, and the resistance of the one-way check valve of the prosthesis device must all be properly sized to accomodate the lung capacity of the individual to achieve the greatest volume and quality of speech with the least amount of effort to the laryngectomee.

Briefly, the present invention provides several significant improvements in a voice prosthesis device which solve many of the problems laryngectomees encounter every day such as: mucus from the lungs getting into the device, impediment of the tubular housing within the esophagus, dilation of the tracheal-esophageal fistula, life of the housing and replacement of the one-way valve assembly within the device, and sizing of the valve bore to each individual lung capacity.

These improvements will greatly enhance the speaking ability of the laryngectomee and permit a quality of life heretofore unavailable to laryngectomees.

Accordingly, one embodiment of the present invention is directed to a tracheoesophageal voice prosthesis device, comprising, a generally cylindrical tapered housing having a bore therethrough, readily removable valve means operably connected within the housing, and a retainer readily connectable within the housing to retain the valve means within the housing. The housing includes a large diameter end having an inner threaded surface portion which terminates in an inner grooved surface portion wherein the valve means are operably disposed adjacent the inner grooved surface portion, a small diameter end, and a tapered transition portion connecting the large diameter end and the small diameter end, and a collar radially outwardly extending from a terminating point of the small diameter end, wherein the collar is characterized to be of a size and shape to allow for relative easy and painless insertion into a tracheal-esophageal fistula while cooperating with the tapered transition portion to provide retention of said device in esophageal tissue surrounding the fistula and substantially prevent movement of the device therethrough.

Another embodiment of the present invention is directed to a voice prosthesis tool for use in positioning a voice prosthesis device into a tracheal-esophageal fistula while minimizing damage to the device, which comprises a generally cylindrical member having one end of a small enough diameter size and sufficient length to enable passing the end through a bore extending through the device and further characterized to have a rounded aspect, and another end of a larger diameter than the bore of the device to prohibit passage therein.

The following accompanying drawings reveal the detailed descriptions of the preferred embodiments of the present invention whereby a more complete understanding of the nature and scope of the invention are now referred.

LIST OF REFERENCE NUMERALS

Figure 1:
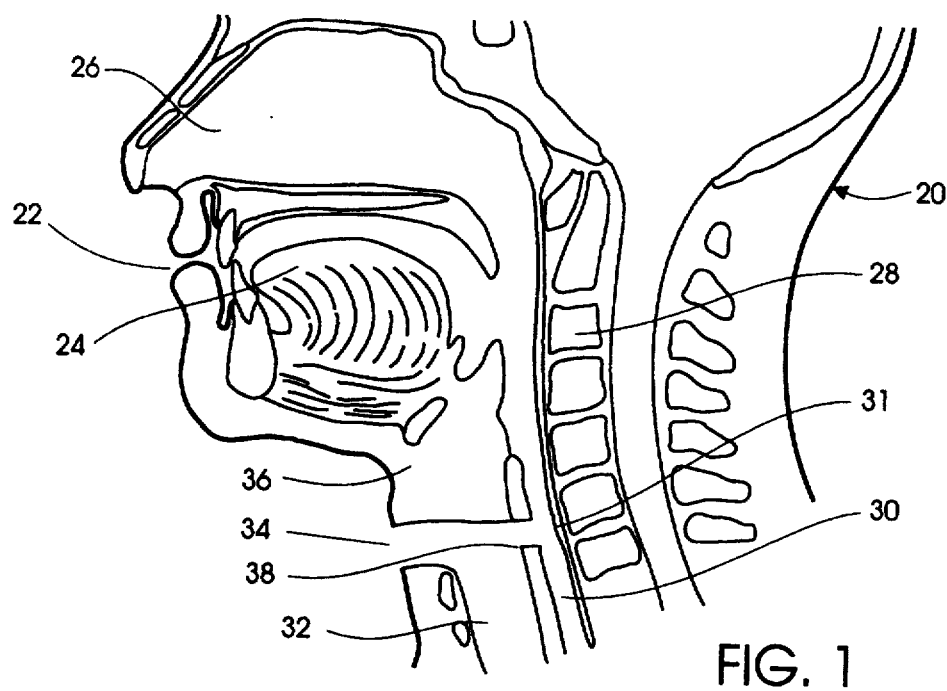
FIG. 1 is a partial sectional view of a post-laryngectomy patient showing a surgically created tracheostoma and a tracheal-esophageal fistula.

NUMERAL PART NAME
20 post-laryngectomy patient having a surgical created tracheostoma and a tracheal-esophageal fistula
22 patient mouth
24 patient's tongue
26 patient's nasal passages
28 patient's spinal column
30 esophagus
31 rear esophageal wall
32 trachea
34 stoma or tracheostoma or open upper end
36 layer of muscle tissue
38 tracheal-esophageal fistula or fistula
40 present invention or prosthesis device or device or voice prosthesis
42 tubular body or tubular housing or housing
44 forward end of housing or trachea end of housing
46 rearward end of housing or esophagus end of housing
47 tapered transition portion
48 retention collar
49 threaded inner surface
50 valve retainer bore section or trachea end bore section
51 grooved surface portion
52 larger in diameter valve flapper bore section or valve bore section
54 rearward housing bore section or esophagus end bore section
56 valve assembly retainer or valve retainer
57 threaded external surface portion
58 valve washers
60 one-way check valve or check valve
62 one-way check valve flapper or valve flapper
64 check valve assembly or valve assembly
66 valve flapper seat shoulder or valve seat shoulder
68 air outlet or opening in esophagus
70 insertion tool or tool
72 enlarged gripping end or handle end
74 gripping ring hole
76 shoulder
78 rounded end projection or rounded projection

DESCRIPTION OF THE PREFERRED EMBODIMENTS

The preferred embodiments of the present invention will now be described as shown throughout the several drawings.

With the removal of the larynx necessitated by injury, trauma, or various types of diseases such as cancer, the trachea may not be left connected with an opening below the rear of the throat because foods, liquids and saliva which are swallowed would tend to travel into the trachea and downward into the lungs causing severe coughing or asphyxiation. This problem is alleviated by making an surgically created opening in the neck to the trachea which is now the breathing opening or tracheostoma for the post-laryngectomee and the trachea is completely out of communication with the esophagus.

Referring to FIG. 1, a numeral 20 generally designates the post-laryngectomy patient with a surgically created tracheostoma or stoma 34 and a tracheal-esophageal fistula 38. The patient's trachea 32 has an open upper end or stoma 34 which is located at the front of the neck. A numeral 22 designates the patient's mouth, a numeral 24 designates the patient's tongue, a numeral 26 designates the patient's nasal passages, a numeral 28 designates the patient's spinal column, a numeral 30 designates the patient's esophagus and a numeral 36 designates the patients layer of muscle tissue.

Figure 2:
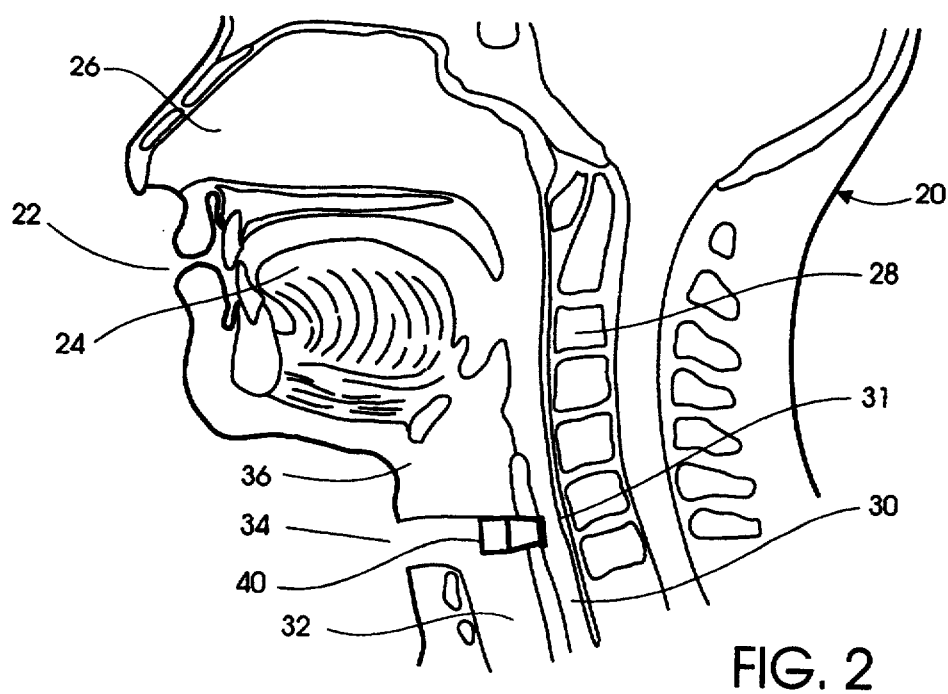
FIG. 2 is a perspective view of the tracheoesophageal voice prosthesis device after being placed in the trachea and inserted through the tracheal-esophageal fistula into the esophagus in accordance to FIG. 1.
Figure 3:
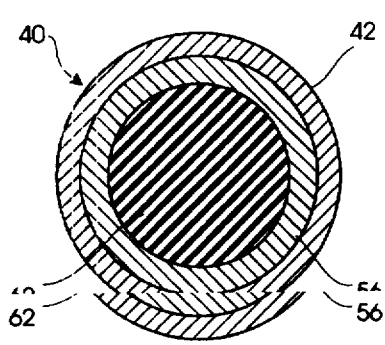
FIG. 3 is the front view of the voice prosthesis device forward end shown in FIG. 2.

As shown in FIGS. 2-5, a prosthesis device or device 40 includes a tapered tubular body or housing 42 and is constructed from a biocompatible material such as implant grade 316 annealed stainless steel per ASTM specification A240 or titanium material of known type. The voice prosthesis 40 has a generally cylindrical forward end 44 of a predetermined diameter which is small enough to enable placement through the stoma 34 but of a sufficient size to allow airflow therethrough when the device 40 is located in the trachea 32. The housing 42 also includes a generally cylindrical rearward end 46 which is of a smaller diameter than the diameter of the forward end 44 and is positioned inside the esophagus 30 (FIG. 2). A tapered transition portion 47 of the housing 42 connects the ends 44 and 46. Attached to the forward end 44 of the tubular housing 42 is a prosthesis retainer (not shown) which may be used to give additional support to position the device within the trachea 32. A collar 48 extends radially outwardly from the end 46. The housing 42 has a threaded inner surface 49 extending axially inwardly from the forward end 44 and terminates in a grooved surface portion 51.

When the device 40 has been inserted through a tracheal-esophageal fistula 38, the retention collar 48 abuts and engages a seal against the esophagus inner forward wall and remains completely within the esophagus 30 while being worn. Once the device 40 has been properly positioned in the patient 20, the device 40 will remain in its position and prevent from becoming accidentally dislodged. The tapered transition portion 47 and the rearward end 46 cooperate in a manner such that the rearward end 46 of the present invention 40 will not come in contact with the rear esophagus wall 31 while being worn, thus the speaking process, swallowing of foods and pills, or drinking liquids is not now impeded.

Figure 4:
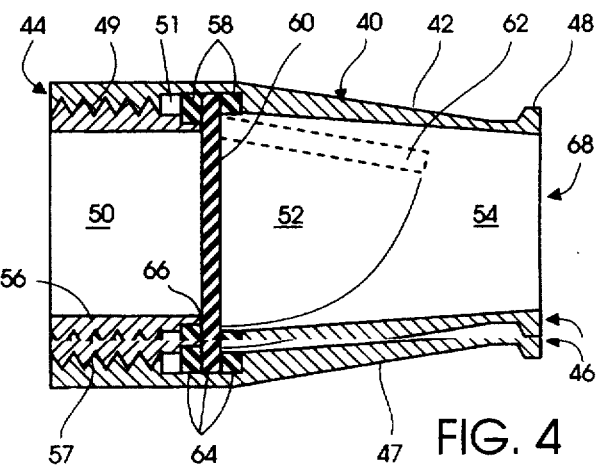
FIG. 4 is a longitudinal sectional view of the present invention of FIG. 3.
Figure 5:
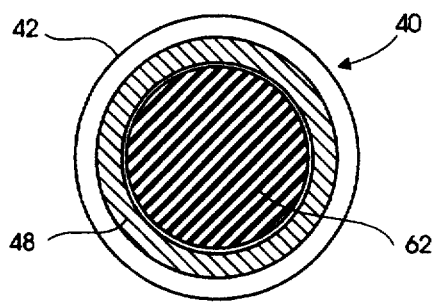
FIG. 5 is a end view of the present invention corresponding to FIG. 4.

Referring particularly to FIG. 4, it will be seen that the bore extending through the tubular housing 42 and has three different bore sections designated at 50, 52, 54. Tracheal-esophageal speech occurs when a finger, thumb or tracheostoma valve covers the opening to the stoma 34 (not shown) to divert the exhaled air from the lungs to the trachea 32 and through the valve retainer bore section 50, thereby pushing the one-way check valve flapper 62 away from the valve seat shoulder 66 to the open position (as shown in dotted lines) within the tubular housing 42; then, the exhaled air passes into the larger in diameter valve flapper bore section 52, thus continuing to the rearward housing bore section 54 and exits at the air outlet 68 or opening in the esophagus 30 to facilitate speech as is known in the art.

Figure 6:
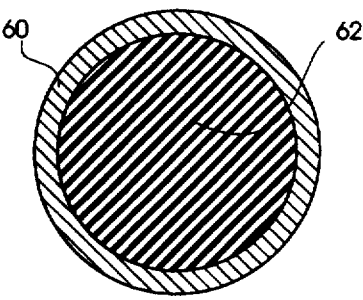
FIG. 6 is a enlarged view of the replaceable one-way check valve of the voice prosthesis corresponding to FIG. 4.

The one-way check valve or check valve 60 (FIGS. 4 and 6) is constructed from a reinforced medical-grade silicone rubber subdermal material which prevents the one way valve flapper or valve flapper 62 from herniating beyond the valve seat shoulder 66 when the pressure within the esophagus increases, such as happens during the production of a hiccup or belch. The check valve 60 is positioned inside the grooved surface portion 51 of the tubular housing 42 with the aid of two valve washers 58 which are constructed of teflon or a similar material. Due to the miniature size of the one-way check valve 60 within the tubular housing 42, the valve washers 58 are glued or attached to the check valve 60 for additional support of the check valve 60 prior to being positioned into the housing 42. Thus, the valve washers 58 and the check valve 60 in combination become the valve assembly 64.

The valve flapper 62 of the check valve 60 becomes unseated or open during the speech process, and at other times closes off the communication between the esophagus 30 and the trachea 32. Thus, when closed, the one-way valve flapper 62 prevents the flow of esophageal material from the esophagus 30 into the trachea 32. The tubular housing 42 protects the valve flapper 62 during its opening and closing excursion from esophageal material. The valve flapper 62 is further seated against the valve seat shoulder 66 during normal swallowing by the patient to insure an effective one-way valve in the closed position.

The one-way check valve 60 and the valve washers 58 are all secured within the tubular housing 42 by the valve assembly retainer or valve retainer 56. The retainer 56 has an external surface portion 57 threaded in a complementary manner to the inner threaded surface 49 of the housing 42. The valve retainer 56 is constructed from a biocompatible material such as implant grade 316 annealed stainless steel per ASTM specification A240, titanium, or injection molded medical-grade silicone rubber subdermal material. Respectively, it is understood that the valve assembly retainer 56 may be constructed in various configurations to obtain the same function as above stated and shown in the drawings, but this is not considered limited to the scope of the present invention.

The valve retainer 56 is easily removed and replaced from the tubular housing 42 with the aid of the valve assembly retainer tool (not shown). The valve retainer 56 includes a valve retainer bore section or trachea end bore section 50 and a valve seat shoulder 66. The tracheal end bore section 50 may be enlarged or reduced to accomodate to each individuals lung capacity, thereby permitting the correct quantity of air to pass from the trachea 32 into the esophagus 30 to produce the best possible speech.

In practice, it has been found that one of the main concerns and a problem laryngectomees experience is that the single one-way valve begins to leak esophageal material into the trachea 32 after having been worn for only a very few weeks. This problem has been solved by lengthening the tubular housing 42 and adding an additional valve section adjacent to the one shown in FIG. 4 (second valve assembly not shown) which greatly extends the length of time that the voice prosthesis 40 can be worn and gives the wearer a feeling of additional security in that esophageal material will be less likely to pass through both valves and into the lungs. However, due to the limited area within the trachea 32 and having to extend the housing 42 to accomodate a second valve assembly area, this double one-way check valve voice prosthesis device may only be worn by persons having larger diameter necks and trachea 32.

Figure 7:
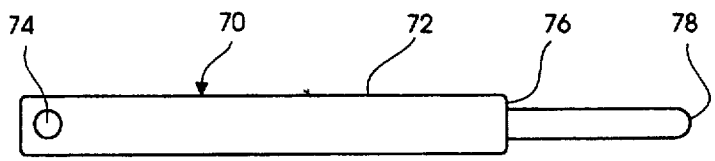
FIG. 7 is a longitudinal view of the insertion tool used to position the tracheoesophageal voice prosthesis in a post-laryngectomy patient.
Figure 8:
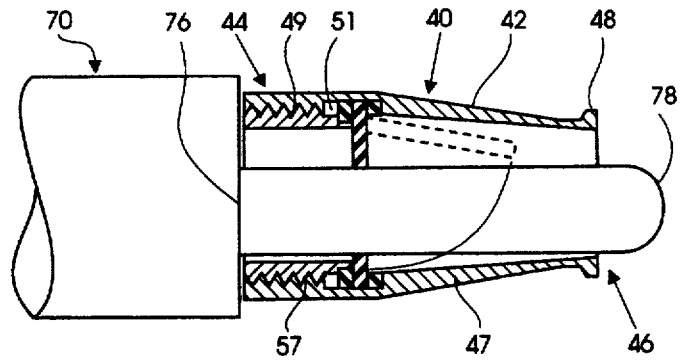
FIG. 8 is a partial sectional view of the device having the insertion tool therein.

FIGS. 7 and 8 show a insertion tool 70 and its placement within the voice prosthesis 40. The insertion tool or tool 70 is particularly useful in positioning the rearward end 46 and the retention collar 48 of the voice prosthesis 40 through a small, normal or misaligned tracheal-esophageal fistula 38 to communicate the trachea 32 and the esophagus 30. The insertion tool 70 includes a gripping ring hole 74 at the enlarged gripping or handle end 72 should user choose to install a key ring (not shown) for additional handle support and having a shoulder 76 with a rounded projection 78 at its rearward end.

The forward end 44 of the tubular housing 42 is adapted to cooperate and engage the end of the shoulder 76 adjacent to the enlarged handle end 72 when the device 40 is inserted into the tracheal-esophageal fistula 38. With the aid of the tool 70 in combination with the unique tubular housing 42 design it is now unnecessary to exert the amount of force that has been previously required to push the prosthesis through the fistula 38 that past devices demanded and the amount of bleeding and pain has now been reduced to a minimum. The rounded end projection 78 of the insertion tool 70 extends through the bore sections 50, 52, 54 and pushes the one-way valve flapper 62 upward within of the housing 42 without causing any damage to the valve flapper 62. Further, misaligned fistulae are easily located with the rounded end projection 78 of the tool 70 during the positioning process of the voice prosthesis 40. This reduces irritation and bleeding of the tracheal-esophageal fistula 38 and the wearer is not subjected to unnecessary coughing discomfort as these areas are very sensitive within the neck.

In summary and other significant advantages of the present invention 40 are that it is self-contained within the trachea 32 and esophagus 30. The prosthesis device 40 substantially limits expelled mucus material from the lungs into the device 40 and it minimizes foreign restrictions within the esophagus 30 that impede the speaking process, or swallowing food or pills, and liquids. The device 40 allows dilation of a small, normal, or misaligned tracheal-esophageal fistula 38 during inserting and prior to removing the prosthesis 40 with the aid of the prosthesis insertion tool 70. The prosthesis device 40 can be easily removed to be cleaned in warm running water to remove encrustations and may be easily replaced by the laryngectomee. The invention is such that the construction material of the tubular housing 42 can be used for many years with the one-way check valve(s) 60 being replaceable and the bore size of the valve retainer 56 may be enlarged or reduced to accomodate each individuals lung capacity and enhance the laryngectomees voice.

Furthermore, the present invention allows the wearer a nearly effortless way to speak with a voice quality as near to normal as possible.

It is believed and clearly understood that person's skilled in this art will readily appreciate the various improvements, modifications and alterations that are made in the preferred embodiments of the present invention which are illustrated and described herein. It is intended that the spirit and scope of the invention be limited not by this detailed description, but rather by the appended claims and their legal equivalents.

What is claimed is:

1. A tracheoesophageal voice prosthesis device, comprising:
   a generally cylindrical tapered housing having a bore therethrough, wherein said housing includes a large diameter end having an inner threaded surface portion which terminates in inner grooved surface portion, a small diameter end, and a tapered transition portion connecting said large diameter end and said small diameter end, and a collar radially outwardly extending from a terminating point of said small diameter end, wherein said collar is characterized to be of a size and shape to allow for relative easy and painless insertion into a tracheal-esophageal fistula while cooperating with said tapered transition portion to provide retention of said device in esophageal tissue surrounding the fistula and substantially prevent movement of said device therethrough;
   readily removable valve means operably connected within said housing, wherein said valve means are operably disposed adjacent said inner grooved surface portion; and
   a retainer readily connectable within said housing to retain said valve means.

2. The device of claim 1, wherein said valve means includes a check valve operably disposed adjacent said inner grooved surface portion of said large diameter end, and a bearing adjacent said grooved surface portion and between one side of said check valve and a portion of said retainer.

3. The device of claim 2, wherein said retainer has a surface portion threaded in a complimentary manner to said inner threaded surface portion of said housing for retaining said check valve and said bearing within the housing when threaded thereto.

4. The device of claim 2, wherein said valve means further includes another bearing disposed adjacent said grooved surface portion of said large diameter end and another side of said check valve.

5. The device of claim 2, wherein said grooved surface portion is generally annular, said check valve is of a flexible material having a generally annular seat portion and a generally circular cover hingedly connected to said seat, and wherein said bearing is a washer.

6. The device of claim 3, wherein said retainer is generally cylindrical.

7. The device of claim 1, wherein said retainer has a surface portion threaded in a complimentary manner to said inner threaded surface portion of said housing for retaining said valve means within said housing when threaded thereto.

8. A tracheoesophageal voice prosthesis device, comprising:
   a generally cylindrical tapered housing having a bore therethrough, said housing having a large diameter end with an inner threaded surface portion terminating in a groove, a small diameter end, a tapered transition portion connecting said large diameter end and said small diameter end, and a collar radially outwardly extending from a terminating point of said small diameter end, wherein said collar is characterized to be of a size and shape to allow for relative easy and painless insertion into a tracheal-esophageal fistula while cooperating with said tapered transition portion to provide retention of said device in esophageal tissue surrounding the fistula and prevent unwanted movement of the device therethrough;
   readily removable valve means operably disposed within said groove of said housing; and
   a generally cylindrical retainer having an outer surface portion threaded in a complimentary manner to said inner threaded surface portion of said large diameter end to allow connection to said housing to retain said valve means within said housing when connected to said housing.

9. The device of claim 8, wherein said valve means includes a check valve operably disposed adjacent said inner grooved surface portion of said large diameter end, and a bearing adjacent said grooved surface portion and between one side of said check valve and a portion of said retainer.

* * * * *